(12) United States Patent
Nakatomi et al.

(10) Patent No.: US 8,897,882 B2
(45) Date of Patent: Nov. 25, 2014

(54) ELECTRODE FOR CONTINUOUSLY STIMULATING FACIAL NERVE ROOT AND APPARATUS FOR MONITORING ELECTROMYOGRAMS OF FACIAL MUSCLES USING THE ELECTRODE THEREOF

(76) Inventors: Hirofumi Nakatomi, Tokyo (JP);
Hidemi Miyazaki, Tokyo (JP)

( * ) Notice: Subject to any disclaimer, the term of this patent is extended or adjusted under 35 U.S.C. 154(b) by 165 days.

(21) Appl. No.: 12/725,928

(22) Filed: Mar. 17, 2010

(65) Prior Publication Data
US 2010/0241203 A1    Sep. 23, 2010

(30) Foreign Application Priority Data
Mar. 18, 2009  (JP) ................... 2009-066214

(51) Int. Cl.
*A61N 1/18*  (2006.01)
*A61N 1/05*  (2006.01)
*A61N 1/36*  (2006.01)
*A61B 5/0492*  (2006.01)

(52) U.S. Cl.
CPC .......... *A61N 1/0558* (2013.01); *A61N 1/36003* (2013.01); *A61B 5/0492* (2013.01)
USPC ........................................... 607/48; 607/116

(58) Field of Classification Search
CPC ......... A61N 1/04; A61N 1/05; A61N 1/0504; A61N 1/0526; A61N 1/0551; A61N 1/0558; A61N 1/36003; A61N 1/36014; A61B 5/0488; A61B 5/0492; A61B 5/4029; A61B 5/4052; A61B 5/4519; A61B 5/4538; A61B 5/683; A61B 5/6846; A61B 5/6877; A61B 5/6882
USPC ........ 607/2, 48, 115, 116, 126, 130; 600/378, 600/546
See application file for complete search history.

(56) References Cited

U.S. PATENT DOCUMENTS 4,155,353 A * 5/1979 Rea et al. .................. 600/380
4,706,682 A * 11/1987 Stypulkowski et al. ...... 600/379
(Continued)

FOREIGN PATENT DOCUMENTS

WO    2006/135751 A2    12/2006
WO    2008/112341 A1    9/2008

OTHER PUBLICATIONS

Michihiro Kohno and Makoto Taniguchi, "Intraoperative Facial Nerve Monitoring During Removal of Acoustic Neuromas and Other Cerebellopontine Angle Tumors", Clinical Electroencephalography, 50 (8), 2008, pp. 449-454.

(Continued)

*Primary Examiner* — Carl H Layno
*Assistant Examiner* — Eugene Wu
(74) *Attorney, Agent, or Firm* — Squire Patton Boggs (US) LLP

(57) ABSTRACT

An electrode for continuously stimulating a facial nerve root capable of a stable holding required for an electrode that continuously stimulates a facial nerve root, and an apparatus for monitoring electromyograms of facial muscles using the electrode for continuously stimulating the facial nerve root, are provided. The electrode for continuously stimulating the facial nerve root comprises an electrode unit, a contact unit, a guard unit, an extension unit, and a wire unit. The electrode for continuously stimulating the facial nerve root is held by clamping the extension unit between the facial nerve root and the anterior inferior cerebellar artery or the small artery so that the contact unit closely contacts to the facial nerve root and is fixed.

6 Claims, 15 Drawing Sheets

(56) References Cited

U.S. PATENT DOCUMENTS

| | | | |
|---|---|---|---|
| 4,796,643 A * | 1/1989 | Nakazawa et al. | 607/128 |
| 4,883,070 A * | 11/1989 | Hanson | 607/116 |
| 6,175,769 B1 * | 1/2001 | Errico et al. | 607/117 |
| 6,308,105 B1 | 10/2001 | Duysens et al. | |
| 6,334,068 B1 | 12/2001 | Hacker | |
| 2001/0031916 A1 * | 10/2001 | Bennett et al. | 600/546 |
| 2004/0176831 A1 * | 9/2004 | Gliner et al. | 607/142 |
| 2005/0137472 A1 * | 6/2005 | Ryu et al. | 600/372 |
| 2006/0041300 A1 * | 2/2006 | Zhang et al. | 607/126 |
| 2008/0132982 A1 | 6/2008 | Gerber | |
| 2008/0183224 A1 | 7/2008 | Barolat | |

OTHER PUBLICATIONS

European Search Report application No. 10250507.0 dated Jul. 28, 2010.

* cited by examiner

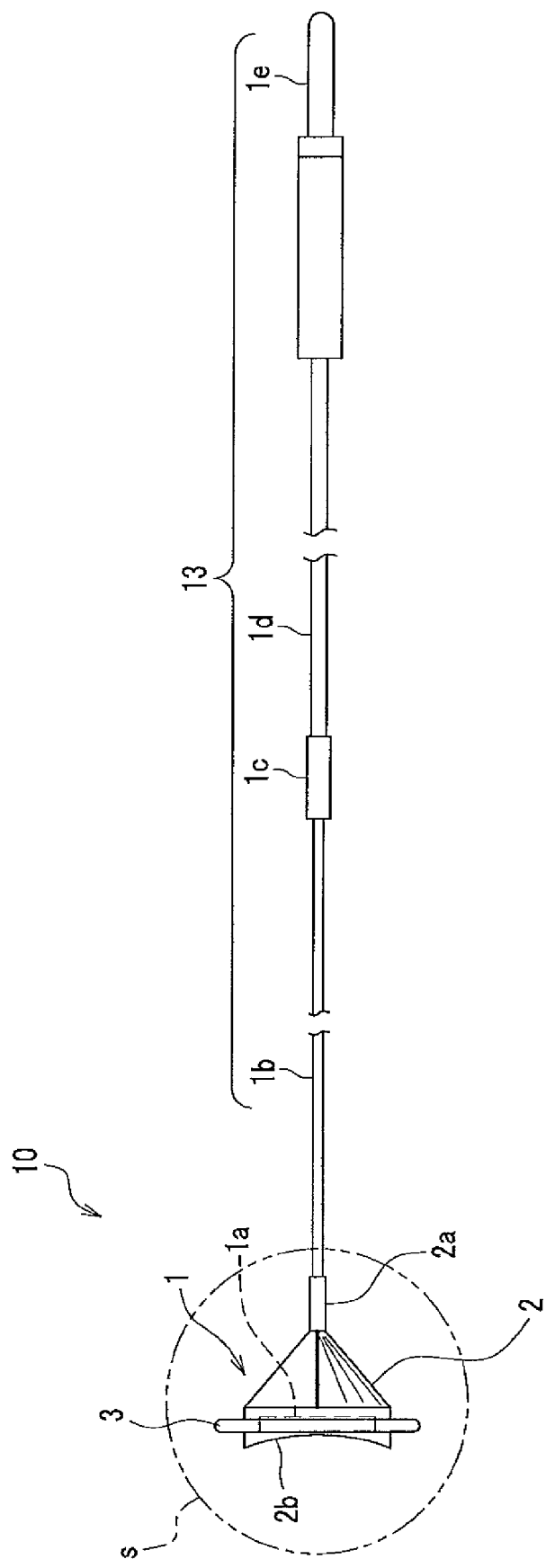

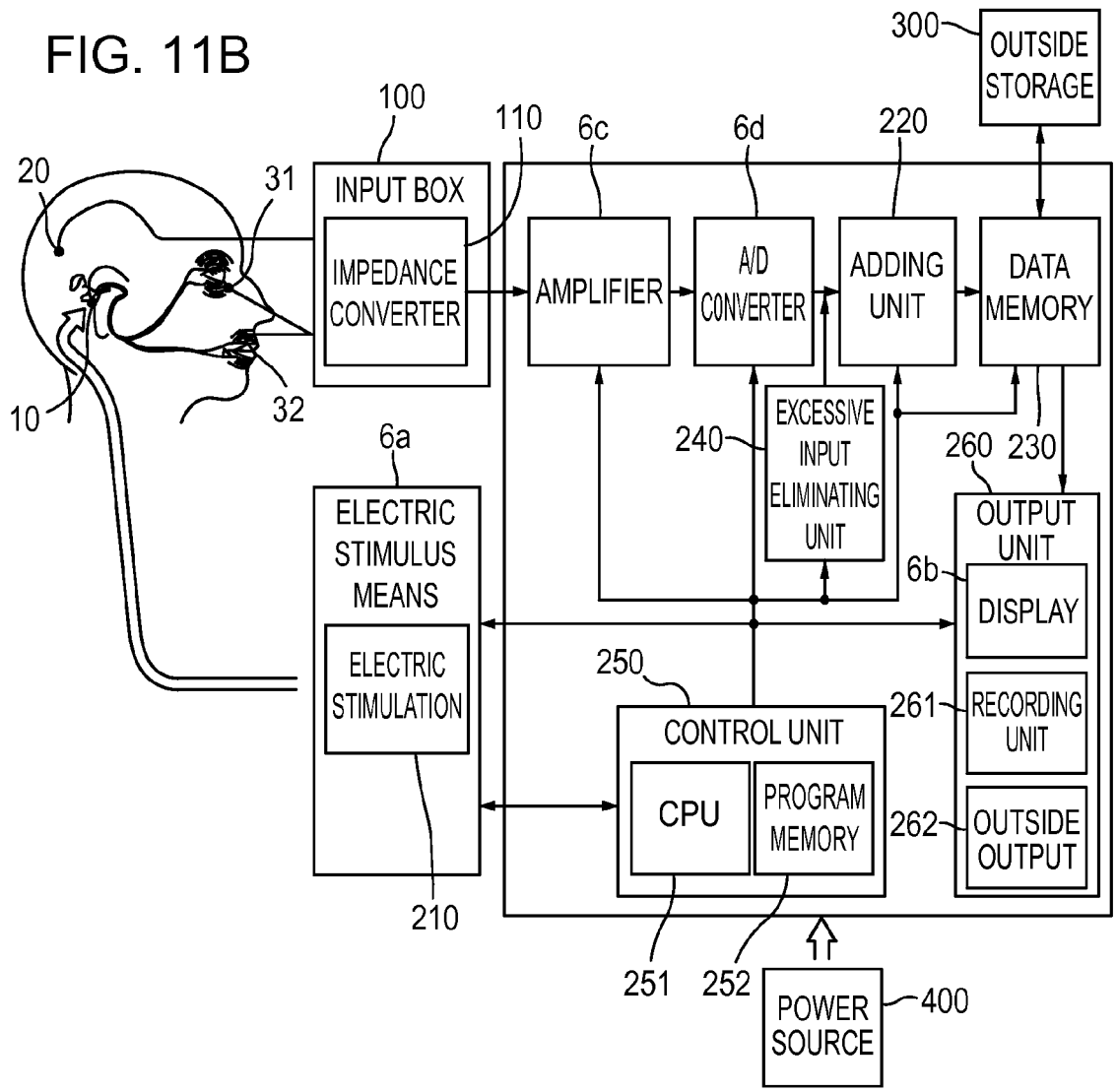

ELECTRODE FOR CONTINUOUSLY STIMULATING FACIAL NERVE ROOT AND APPARATUS FOR MONITORING ELECTROMYOGRAMS OF FACIAL MUSCLES USING THE ELECTRODE THEREOF

CROSS REFERENCE TO RELATED APPLICATION

This application claims priority under 35 U.S.C. §119 to Japanese Patent Application No. 2009-066214, filed on Mar. 18, 2009. The subject matter of this application is hereby incorporated by reference.

BACKGROUND OF THE INVENTION

1. Field of the Invention

The present invention relates to an electrode for continuously stimulating a facial nerve root and an apparatus for monitoring electromyograms of facial muscles using the electrode thereof.

2. Description of Related Art

A facial nerve is one of the twelve cranial nerves, called the seventh cranial nerve. The facial nerve regulates movements of "facial muscles" which make facial expressions. Muscles covering a face are regulated by a thick nerve, that is, the facial nerve.

FIG. 13 is an enlarged diagram showing the facial nerve which branches into four leading to human facial muscles. As shown in FIG. 13, the facial nerve H extending from a facial nucleus G in a brain, comes out of an inside of a right ear, and reaches facial muscles such as an orbicularis oculi muscle J around a right eye and an orbicularis oris muscle K around a right mouth.

FIG. 14 is an enlarged diagram showing the facial nerve H of FIG. 13. As shown in FIG. 14, it is observed that nerve fibers of the facial nerve H arise from the facial nucleus G, and pass behind a neighboring auditory nerve L. The facial nerve H comprises a facial nerve H1 located inside a brainstem, a facial nerve root H2 which is a root of the facial nerve coming out of the brainstem, a facial nerve H3 located in a cerebral cistern, and a facial nerve H4 located in a temporal bone as shown in FIG. 14.

FIG. 15 is a perspective view showing a conventional bell shaped electrode described in a non-patent document. M. Kohno and M. Taniguchi, "Intraoperative facial nerve monitoring during removal of acoustic neuromas and other cerebellopontine angle tumors", Clinical Electroencephalography, 50 (8), 449-454, 2008/8. FIG. 16 is a diagram showing a state that the conventional bell shaped electrode is placed in a lesion part.

As shown in FIG. 15, the conventional bell shaped electrode 16 is formed spherical, including an upper portion which has a bell type shape, and a lower portion which is formed as a hemispherical contact portion. Here, FIG. 16 shows a state that the bell shaped electrode 16 is placed at a starting part of the facial nerve so as to contact to the starting part thereof and continuously stimulate the facial nerve at a frequency of 1 Hz.

Herein, there is a problem that it is difficult to stably hold the electrode 16 only by dwelling it on the facial nerve because the electrode 16 is formed spherical having a bell type shape. Further, since the bell shaped electrode 16 is prone to be moved when a minute force is applied to a lead wire (electrical cord), there is a problem that it is difficult to continuously stimulate a definite region of the facial nerve.

Further, there is another problem that it is difficult to stably hold the conventional bell shaped electrode as being adhesive to the facial nerve. The electrode 16 is prone to move and a stimulating position easily shifts.

For these reasons, there is a need for an electrode for continuously stimulating a facial nerve which is capable of more surely stimulating and monitoring the facial nerve than conventional electrodes, and a monitoring apparatus using the electrode thereof.

SUMMARY OF THE INVENTION

The present invention has been developed to solve the above-mentioned problems. It is an object of the present invention to provide an electrode capable of continuously stimulating a root of the facial nerve in order to stably stimulate and monitor the facial nerve function as a whole, and an apparatus for monitoring electromyograms of facial muscles using the electrode for continuously stimulating the facial nerve root.

Herein, the present invention provides an electrode for continuously stimulating a facial nerve root (10), which electrically stimulates the facial nerve root (H2) that is a root of a facial nerve (H) arising from a facial nucleus (G) in a brainstem (F), and monitors electromyograms of contraction responses of an orbicularis oculi muscle (J) and an orbicularis oris muscle (K) which are regulated by the facial nerve (H). The electrode for continuously stimulating the facial nerve root (10) includes an electrode unit (1a) to which weak electric currents electrically stimulating the facial nerve root (H2) are fed, a contact unit (2b) which is electrically connected to the electrode (1a) and contacts to the facial nerve root (H2), a guard unit (2) which covers the electrode (1a) except for the contact unit (2b), and an extension unit (3) which is formed in a thin flake shape extending from a periphery of the guard unit (2). Herein, the electrode for continuously stimulating the facial nerve root (10) is held by clamping the extension unit (3) between the root (H2) of the facial nerve (H) which comes out of the brainstem (F) and an anterior inferior cerebellar artery (M) which passes crossing the facial nerve root (H2), so as to fix the contact unit (2b) to the facial nerve root (H2).

Further, the present invention provides the electrode for continuously stimulating the facial nerve root (10), in which the extension unit (3) is provided on the whole periphery of the guard unit (2).

Further, the present invention provides the electrode for continuously stimulating the facial nerve root (10), in which the extension unit (3) is made of silicon.

Further, the present invention provides the electrode for continuously stimulating the facial nerve root (10), in which the contact unit (2b) is formed as a recess shaped portion (2c), a projection shaped portion (2e), or a flat shaped portion (2f), corresponding to an outer peripheral surface of the facial nerve root (H2).

Further, the present invention provides an apparatus for monitoring electromyograms of facial muscles (12) using the electrode for continuously stimulating the facial nerve root (10). The apparatus for monitoring electromyograms of facial muscles (12) includes the electrode for continuously stimulating the facial nerve root (10), an electric stimulus means (6a) which stimulates the facial nerve root (H2) of a patient on whom the electrode for continuously stimulating the facial nerve root (10) is placed, a display (6b) which displays electromyograms of contraction responses of an orbicularis oculi muscle (J) and an orbicularis oris muscle (K) which are regulated by the facial nerve (H) stimulated by the electrode for continuously stimulating the facial nerve root (10).

According to the present invention, the electrode for continuously stimulating the facial nerve root is held by clamping the extension unit between the facial nerve root which is a root of the facial nerve coming out of the brainstem and the anterior inferior cerebellar artery which passes crossing the facial nerve root, so as to fix the contact unit to the facial nerve root. Hereby, since the facial nerve root is stably stimulated by the electrode thereof, it is possible to monitor contraction responses of an orbicularis oculi muscle and an orbicularis oris muscle by holding the electrode on the facial nerve root which extends from a facial nucleus. Moreover, since a stable holding required for an electrode for continuously stimulating a facial nerve root is achieved, it is possible to provide an electrode for continuously stimulating a facial nerve root capable of performing stable stimulation and monitoring.

According to the present invention, by providing the extension unit on the whole periphery of the guard unit, the extension unit can be flexibly clamped even if there is a positional gap between the facial nerve root which comes out of the brainstem and the anterior inferior cerebellar artery which passes crossing the facial nerve root. Therefore, it is possible to stably stimulate the facial nerve root.

Further, according to the present invention, by forming the extension unit by silicon, the extension unit hardly damages surrounding brain and blood vessels, since silicon which is a biocompatible resin is soft so as to softly contact to the brain and blood vessels. Furthermore, due to the flexibility of silicon of the extension unit, the electrode can be smoothly placed between body tissues and held on the tissues stably.

Further, according to the present invention, the electrode is selected from an electrode having a recess, projection, or flat shaped contact unit, corresponding to an outer peripheral surface of the facial nerve root. Hereby, since the electrode can tightly contact to the facial nerve root, it is possible to provide an electrode for continuously stimulating a facial nerve root having capability of stably stimulating and monitoring the facial nerve root, the capability being required for the electrode for continuously stimulating the facial nerve root.

Furthermore, according to the apparatus for monitoring electromyograms using the electrode for continuously stimulating the facial nerve root of the present invention, it is possible to reduce background noises and obtain clear waveforms which can facilitate the analysis, by using the electrode for continuously stimulating the facial nerve root, which can be easily and stably placed on the facial nerve root. Hereby, the apparatus for monitoring the electromyograms of the facial muscles, which increases recording sensitivity and specificity, can be provided.

BRIEF DESCRIPTION OF THE DRAWINGS

FIG. 1 is a diagram showing a whole structure of the electrode for continuously stimulating the facial nerve root of the present invention.

FIG. 2A, FIG. 2B, and FIG. 2C are left, front, and right side views of the electrode, respectively.

FIG. 3A, FIG. 3B, and FIG. 3C are left, front, and right side views of the electrode, respectively.

FIG. 4A, FIG. 4B, and FIG. 4C are left, front, and right side views of the electrode, respectively.

FIG. 5A shows an electrode part whose contact unit has a recess shaped surface. FIG. 5B shows an electrode part whose contact unit has a projection shaped surface. FIG. 5C shows an electrode part whose contact unit has a flat surface.

FIG. 7A shows the electrode part whose contact unit has a recess shaped surface. FIG. 7B shows the electrode part whose contact unit has a projection shaped surface. FIG. 7C shows the electrode part whose contact unit has a flat surface.

FIGS. 8A, 8B, and 8C show left, front, and right side views of the electrode, respectively.

FIGS. 9A, 9B, and 9C show left, front, and right side views of the electrode, respectively.

FIG. 12A shows a waveform of an orbicularis oculi muscle, and FIG. 12 B shows a waveform of an orbicularis oris muscle.

DETAILED DESCRIPTION OF THE PREFERRED EMBODIMENT

Example 1

As shown in FIG. 1, the electrode for continuously stimulating the facial nerve root 10 includes an electrode part 1 and a wire unit 13.

<<Constitution of Electrode Part>>

Figure 5A:
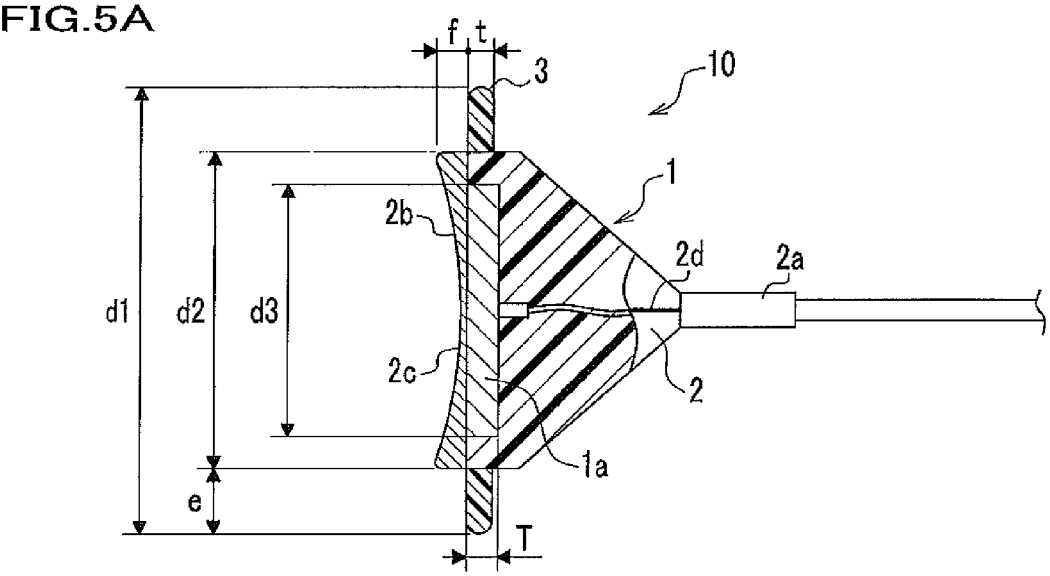
FIGS. 5A to 5C are enlarged cross-sectional diagrams of the electrode for continuously stimulating the facial nerve root of FIGS. 2A to 2C.

FIG. 5A is a cross-sectional view of the electrode part 1 of the electrode for continuously stimulating the facial nerve root 10 shown in FIG. 1. The electrode part 1 of the electrode for continuously stimulating the facial nerve root 10 includes an electrode unit 1*a* which electrically stimulates the facial nerve root H2 (referred to FIG. 6), a contact unit 2*b* which is electrically connected to the electrode unit 1*a* and contacts to the facial nerve root H2, a guard unit 2 which is made of insulation surrounding a periphery of the electrode unit 1*a* as exposing the contact unit 2*b*, and an extension unit 3 which is formed on a periphery of the guard unit 2 as extending from the periphery.

<Electrode Unit>

As shown in FIG. 5A, the electrode unit 1*a* of the present embodiment is an electrode to continuously stimulate a facial nerve root H2, and formed in a thin disk shape. The electrode unit 1*a* is made of, for example, platinum (Pt) foil. The electrode unit 1*a* formed in a thin disk shape, has a diameter "d3" of about 2.0 mm, and a thickness "T" of 0.5 mm. A wire uprises at right angles from the surface of the electrode unit 1*a*.

<Size of Electrode Part>

Figure 2C:
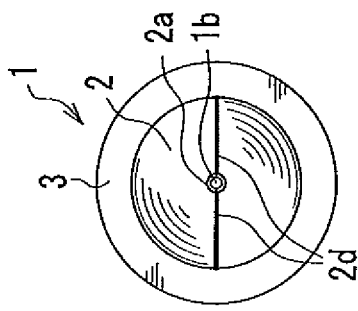
FIGS. 2A to 2C are enlarged diagrams of the electrode part of the electrode for continuously stimulating the facial nerve root of FIG. 1.
Figure 2B:
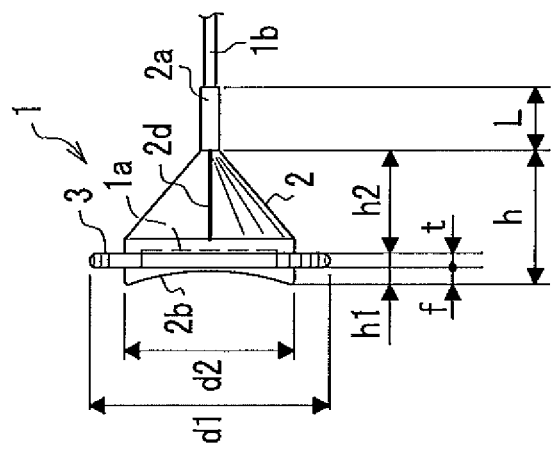
Figure 2A:
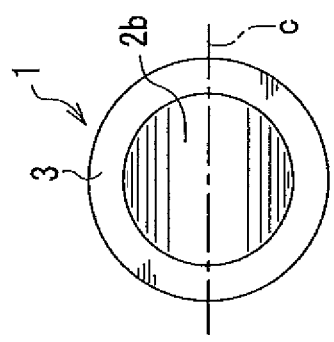
Figure 3C:
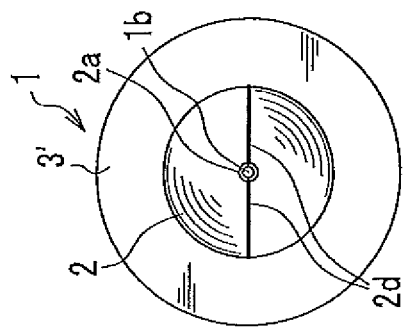
FIGS. 3A to 3C are enlarged diagrams of the electrode part of the electrode for continuously stimulating the facial nerve root of FIG. 1.
Figure 3B:
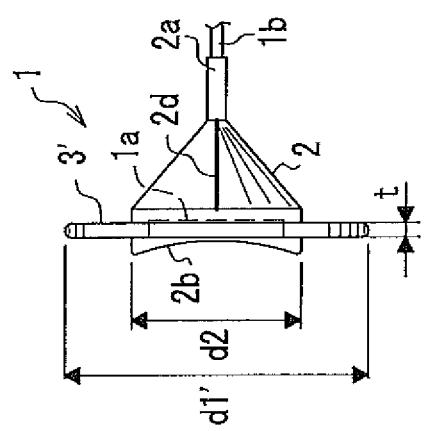
Figure 3A:
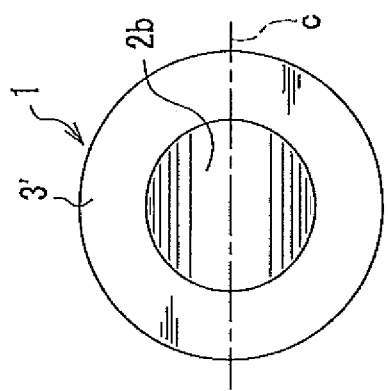
Figure 4C:
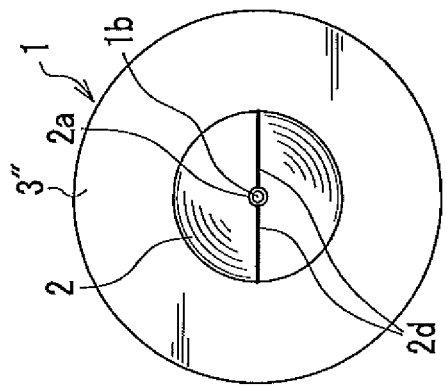
FIGS. 4A to 4C are enlarged diagrams of the electrode part of the electrode for continuously stimulating the facial nerve root of FIG. 1.
Figure 4B:
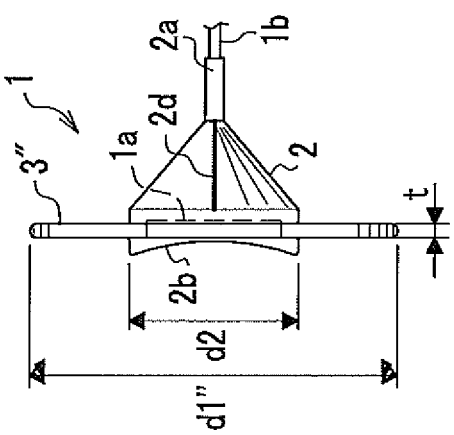
Figure 4A:
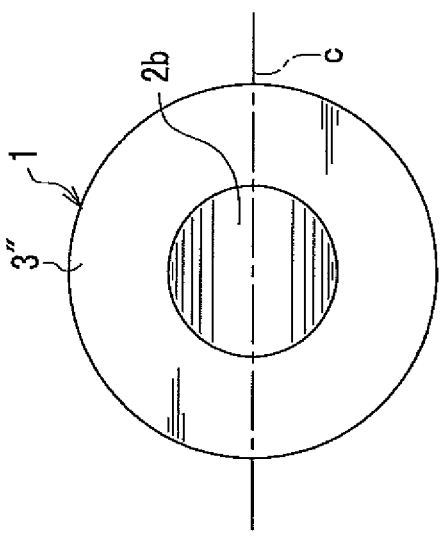

A diameter "d2" of the electrode part 1 is φ2.5 mm, as shown in FIGS. 2B, 3B, and 4B. With respect to heights of the electrode part 1, "h" is about 2.0 mm, "h1" is 0.5 mm, and "h2" is 1.5 mm (referred to FIG. 2B). A thickness "t" of the extension unit 3 is 0.25 mm. A thickness "f" of the contact unit 2*b* is 0.25 mm. Herein, h=h1+h2, and h1=t+f.

Further, as shown in FIG. 2B, a diameter "d1" of the extension unit 3 is 3.5 mm (that is, 2.5 mm of d2+0.5 mm×2).

As shown in FIG. 3B, a diameter "d1'" of the extension unit 3' is 4.5 mm (that is, 2.5 mm of d1+1.0 mm×2).

As shown in FIG. 4B, a diameter "di'" of the extension unit 3" is 5.5 mm (that is, 2.5 mm of d2+1.5 mm×2).

Here, as shown in FIGS. 3B and 4B, the thickness "t" may be formed thicker in a range between 0.25 mm and 0.5 mm, as the diameter of the extension unit 3 is formed thicker.

Here, the shape of the electrode part 1 may be oval or elliptical besides circular.

<Constitution of Contact Unit>

The contact unit 2*b* is electrically connected to the electrode unit 1*a*, and made of a high conductive metal, for example, gold (Au). Since the electric resistance of gold is significantly small, a stable electric stimulation can be provided. Further, in FIG. 5A, the contact unit 2*b* is formed as a recess shaped portion 2*c* corresponding to an outer peripheral surface of the facial nerve root H2 so that the recess shaped portion 2*c* facilitates the contact unit 2*b* more stably contacting to the facial nerve root H2. Preferably, a recessed depth of the recess shaped portion 2*c* is 0.2 mm.

Figure 5B:
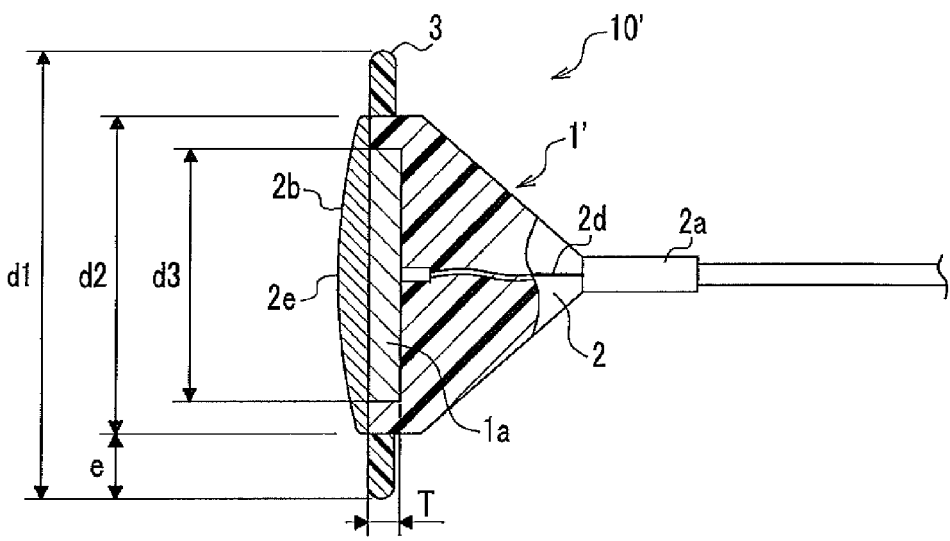

In FIG. 5B, the contact unit 2*b* is formed in a projection shape. A difference of FIG. 5B from FIG. 5A is that the contact unit 2*b* of the electrode part 1' of the electrode for continuously stimulating the facial nerve root 10' is formed as a projection shaped portion 2*e*. Preferably, a projected height of the projection shaped portion 2*e* is in a range between 0.05 mm and 0.2 mm.

Figure 5C:
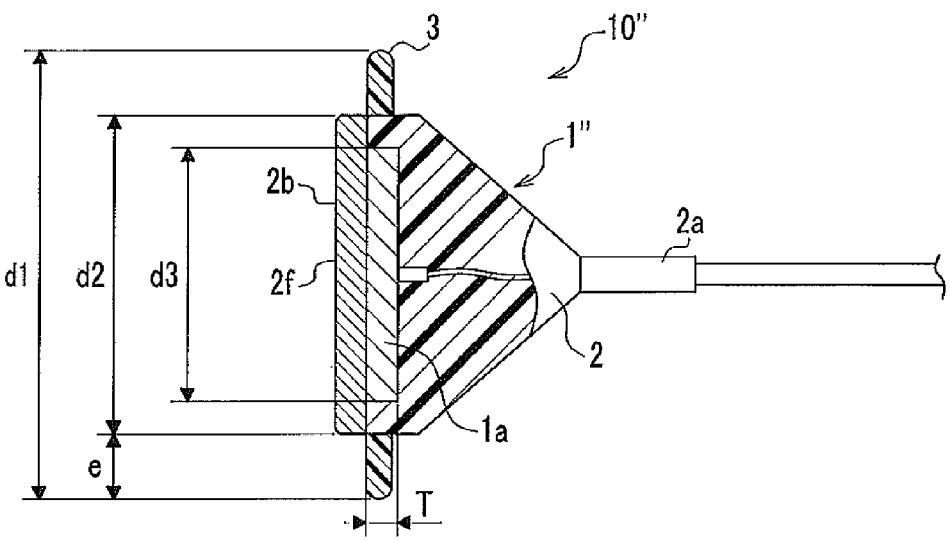

In FIG. 5C, the contact unit 2*b* is formed in a flat shape. A difference of FIG. 5C from FIG. 5A is that the contact unit 2*b* of the electrode part 1" of the electrode for continuously stimulating the facial nerve root 10" is formed as a flat shaped portion 2*f*.

Here, if actual use frequencies of these three different shaped electrodes in the clinic are estimated, the estimated ratio of the electrodes for continuously stimulating the facial nerve root 10, 10', and 10", is about 6:2:2.

<Constitution of Guard Unit>

The guard unit 2 protects the electrode part 1 by covering with an insulation resin, excluding the contact unit 2*b*. As shown in FIG. 5A, a front cross-sectional view of the guard unit 2 is triangular. The guard unit 2 is formed in a conical shape. As shown in FIGS. 2C, 3C, and 4C, a marking 2*d*, which is a line shaped or a dotted line shaped marker, is attached or carved on the guard unit 2. The marking 2*d* is used for adjusting the marker parallel to a direction of an axis "c" of the facial nerve root H2 to which the recess shaped portion 2*c* contacts. Here, a color of the marking 2*d* is yellow since yellow is a color having a largely different brightness from black which is used for the resin of the guard unit 2. However, white, red, green, or other colors may be used for the marking 2*d*. On an outer periphery of a bottom part of the guard unit 2, the extension unit 3 is formed as covering the whole circumferential periphery thereof.

<Constitution of Extension Unit>

As shown in FIGS. 2A to 4C, the extension units 3, 3' and 3" are arranged in a hat brim shape as extending from the whole circumferential periphery of the guard unit 2. The extension unit 3 is made of a biocompatible resin, which is composed of, for example, silicon (or called silicone). Silicon is aggregates formed of organo-silicon compounds and has a sufficient elasticity like rubber. Because of the elasticity, silicon is a preferable material since silicon hardly damages organ tissues when the electrode is inserted and held in a gap of organ tissues. Here, in place of silicon, the extension units 3, 3', and 3" may be made of soft polyurethane resin, soft plastic, or rubber having elasticity as soft as silicon.

Outer peripheries of the extension units 3, 3', and 3" are formed with round corners as shown in FIGS. 2A to 4C.

Herein, the shapes of the extension units 3, 3', and 3" shown in FIGS. 2A to 4C are described as an example for explaining the embodiment. Therefore, another shape, for example, a shape in which a part of the extension unit is cut off, can be used.

<Handle>

A handle 2*a* is a bar shaped unit provided on a top of the guard unit 2 formed in a cone shape. The handle 2*a* is a unit which is pinched by a pair of tweezers (not shown) when the electrode part 1 is inserted and held between organ tissues. A length "L" of the handle 2*a* is in a range between 1.5 mm and 2 mm. Here, a first wire 1*b* extends from a top of the handle 2*a*. Since the handle 2*a* can be pinched easily, it is possible to facilitate the electrode part 1 to be inserted and held.

<Constitution of Wire Unit>

As shown in FIG. 1, a wire unit 13 includes a super-thin first wire 1*b* having a length of 0.5 m, a semi-super-thin second wire 1*d* having a length of about 2.0 m connected through a joint 1*c* to the first wire 1*b*, and a pin tip 1*e* which is a plug connected to the second wire 1*d*.

Here, a thickness of the first wire 1*b* is φ0.4 mm, preferably, in a range between φ0.3 mm and 0.5 mm. The first wire is covered by a red insulation. A thickness of the second wire 1*d* is φ1.2 mm. A length of the second wire 1*d* can be longer or shorter than 2.0 m.

<Holding Place of Electrode Part>

Next, a holding place of the electrode part 1 of the electrode for continuously stimulating the facial nerve root 10 will be explained.

Figure 6:
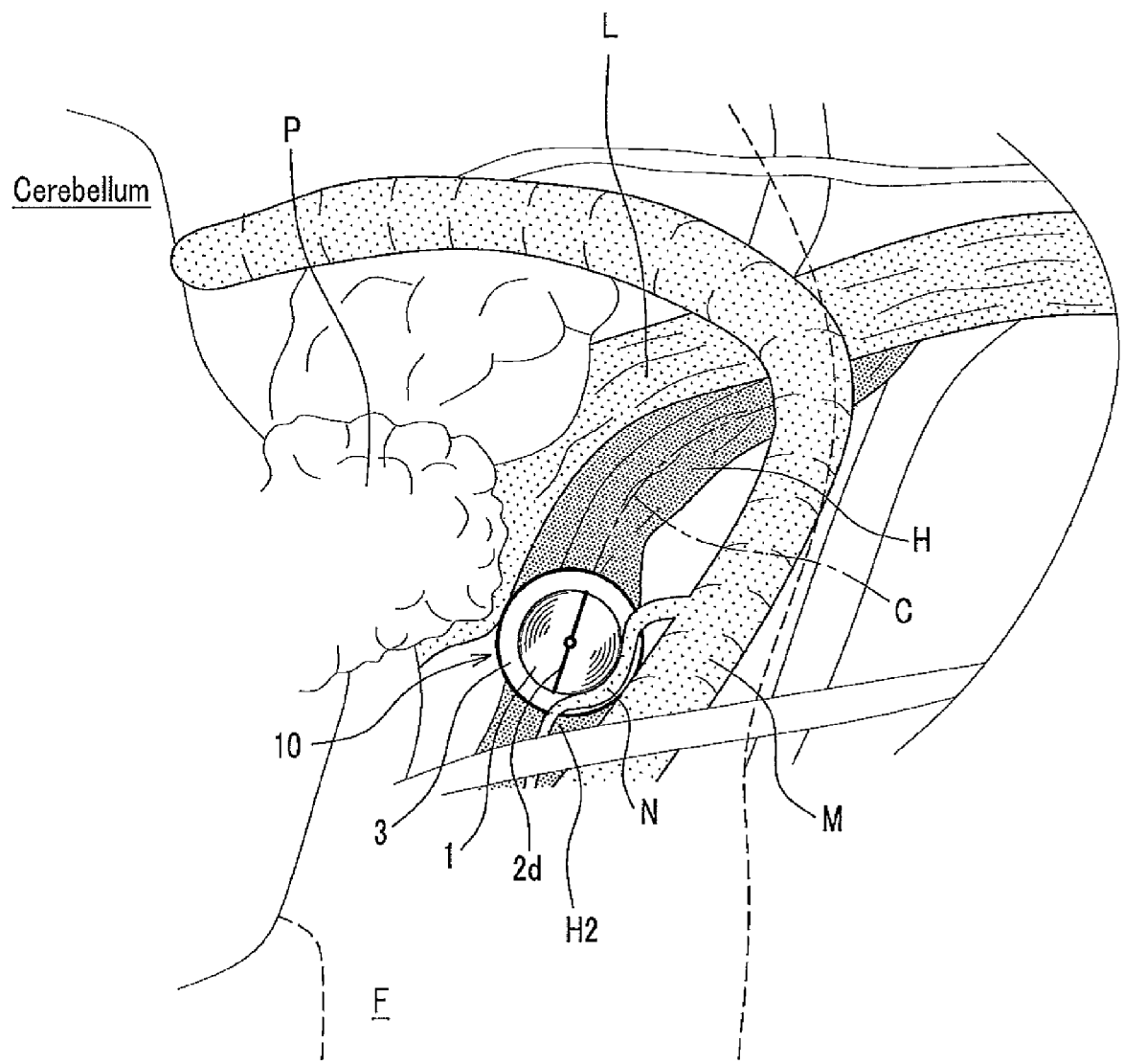
FIG. 6 is an enlarged diagram of the region surrounded by the double dotted line in FIG. 14, which shows a place where the electrode for continuously stimulating the facial nerve root of the present invention is held.

As shown in FIG. 6, the electrode part 1 is held at a place between a root of a facial nerve H just coming out of a brainstem F, that is, a facial nerve root H2, and an anterior inferior cerebellar artery M. Although the anterior inferior cerebellar artery M adheres to the facial nerve root H2 by arachnoid membrane lamellae, the anterior inferior cerebellar artery M can be easily separated from the facial nerve root H2. By separating the anterior inferior cerebellar artery M from the facial nerve root H2, and inserting the extension unit 3 of the electrode part 1 in a gap between the anterior inferior cerebellar artery M and the facial nerve root H2, the electrode part 1 is stably clamped and fixed by this big blood vessel, that is, the anterior inferior cerebellar artery M.

Alternatively, as shown in FIG. 6, the electrode part 1 is held at a place between the root of the facial nerve H just coming out of the brainstem F, that is, the facial nerve root H2, and a small artery N. Although the small artery N adheres to the facial nerve root H2 by arachnoid membrane lamellae, the small artery N can be easily separated from the facial nerve root H2. By separating the small artery N from the facial nerve root H2, and inserting the extension unit 3 of the electrode part 1 in a gap between the small artery N and the facial nerve root H2, the electrode part 1 is stably clamped and fixed by this thin blood vessel, that is, the small artery N.

Herein, it is observed in about 86% probability that at a place where the facial nerve root H2 just comes out of the brainstem F, a big blood vessel (that is, anterior inferior cerebellar artery M) and a small blood vessel (that is, small artery N) are neighboring and pass crossing the facial nerve root H2. Further, it is observed that a choroid plexus P producing cerebrospinal fluid covers a root of an auditory nerve L, and behind the auditory nerve L extending from the cochlear nucleus, the facial nerve H passes.

Since the facial nerve root H2 that is a root of the facial nerve H extending from the facial nucleus G is located at the closest place to the facial nucleus G, the facial nerve root H2 is a preferable place where the electrode part 1 is to be held.

FIG. 6 shows a state that the extension unit 3 of the electrode part 1 is clamped and fixed between the facial nerve root H2 and the small artery N which passes in front of the facial nerve root H2 as crossing it.

The electrode unit 1a with a circular shape is arranged in the center of the electrode part 1. A periphery of the electrode unit 1a is protected by the guard unit 2 in a conical shape. Further, the extension unit 3, which is soft and safe, is formed in a hat brim shape. The electrode part 1 is fixed by holding the extension unit 3 between the small artery N and the facial nerve root H2, or between the anterior inferior cerebellar artery M and the facial nerve root H2. As mentioned above, by providing the extension unit 3 which has not been provided in conventional electrodes, it is possible to provide an electrode part 1 capable of performing a stable electric stimulation. Further, in many cases, the electrode part 1 can be more strongly clamped by the choroid plexus P. Therefore, the electrode part 1 may be fixed by the choroid plexus P.

Here, three typed shapes such as recess, projection, and flat typed shapes are prepared for the contact unit 2b of the electrode part 1, corresponding to the shape of the facial nerve root H2.

Figure 7A:
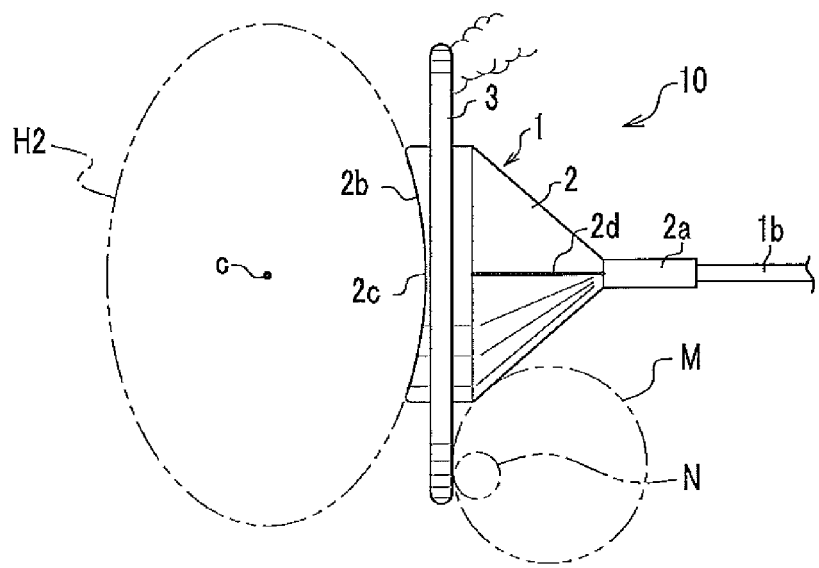
FIGS. 7A to 7C are diagrams showing a state that the electrode for continuously stimulating the facial nerve root of the present invention is held between the facial nerve root and the anterior inferior cerebellar artery or the small artery.

As shown in FIG. 7A, if a cross-section of the facial nerve root H2 is convex, the contact unit 2b having a recess shaped portion 2c can fit to the surface of the facial nerve root H2, corresponding to the convex shaped outer peripheral surface of the facial nerve root H2. This case is an overwhelming majority observed in about 60% in all the cases.

As shown in FIG. 7A, the extension unit 3 of the electrode part 1 is held at a place where the anterior inferior cerebellar artery M passes crossing just in front of the facial nerve root H2. Then, the extension unit 3 is clamped between the facial nerve root H2 and the anterior inferior cerebellar artery M, or between the facial nerve root H2 and the small artery N, and is to be fixed. Further, the extension unit 3 is more strongly clamped by the choroid plexus P and is to be fixed.

Alternatively, the extension unit 3 of the electrode part 1 is held at a place where the small artery N passes crossing just in front of the facial nerve root H2. Then, the extension unit 3 is clamped between the facial nerve root H2 and the anterior inferior cerebellar artery M, or between the facial nerve root H2 and the small artery N, and is to be fixed. Further, the extension unit 3 is strongly clamped by the choroid plexus P and is to be fixed.

Figure 7B:
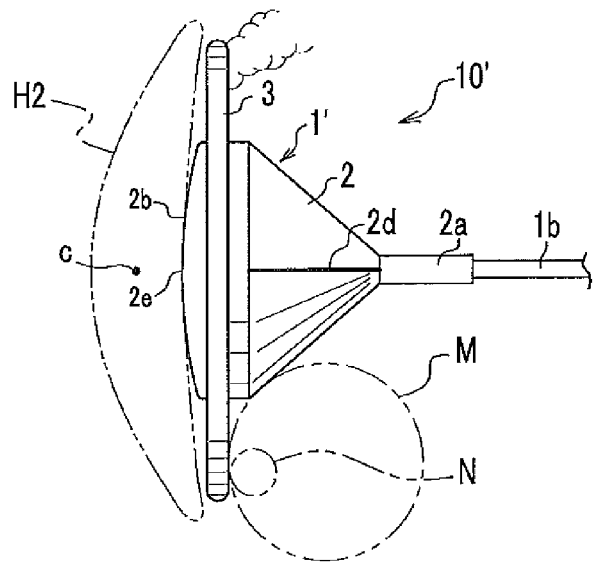

As shown in FIG. 7B, if a cross-section of the facial nerve root H2 is concave, the contact unit 2b having a projection shaped portion 2e can fit to the surface of the facial nerve root H2, corresponding to the concave shaped outer peripheral surface of the facial nerve root H2. This case is observed in about 20% in all the cases.

Figure 7C:
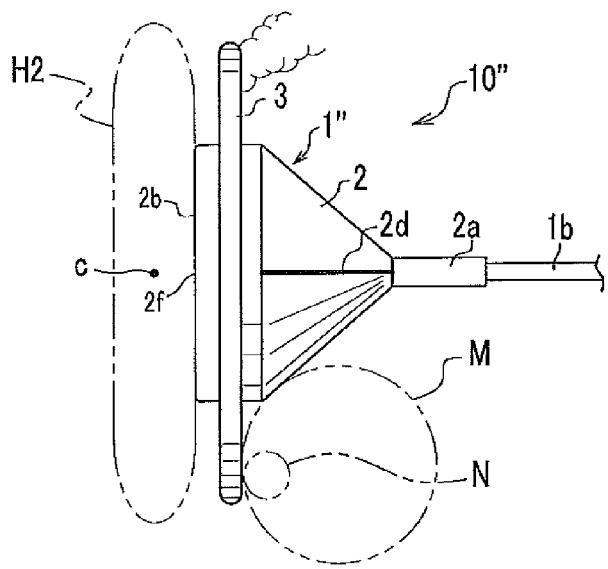

Further, as shown in FIG. 7C, if a cross-section of the facial nerve root H2 is flat, the contact unit 2b having a flat shaped portion 2f can fit to the surface of the facial nerve root H2, corresponding to the flat shaped outer peripheral surface of the facial nerve root H2. This case is observed in about 20% in all the cases.

As a result, it is possible to stimulate all types of facial nerve fibers by the above-mentioned electrodes for continuously stimulating the facial nerve root of the present invention.

Example 2

A difference between Example 1 and Example 2 is a shape of the extension unit 3. Therefore, hereinafter, only the difference will be explained and detailed explanation will be omitted.

Figure 8A:
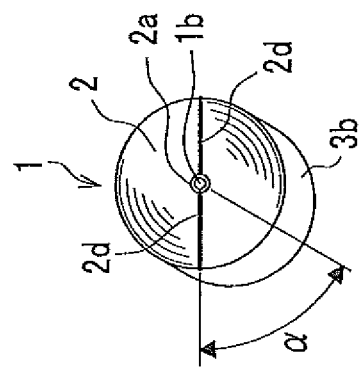
FIGS. 8A to 8C are enlarged diagrams showing another example of the electrode for continuously stimulating the facial nerve root of the present invention.
Figure 8B:
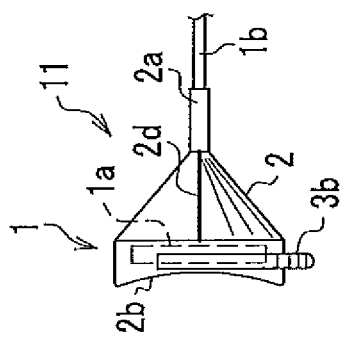
Figure 8C:
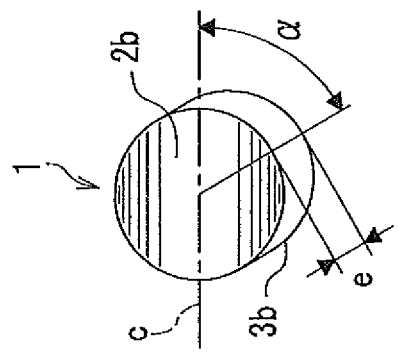
Figure 9C:
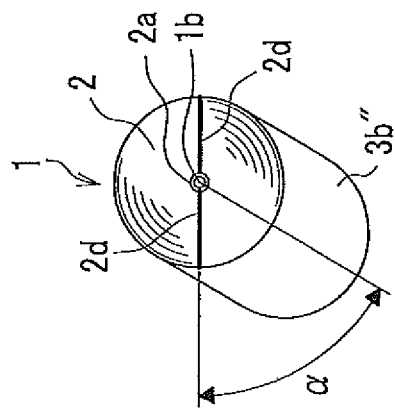
FIGS. 9A to 9C are enlarged diagrams showing another example of the electrode for continuously stimulating the facial nerve root of the present invention.
Figure 9B:
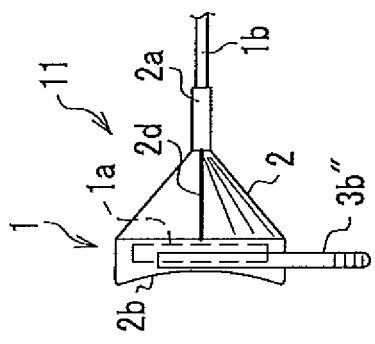
Figure 9A:
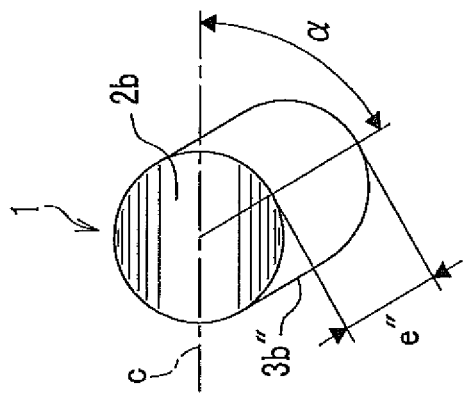

As shown in FIGS. 8A to 8C, Example 2 is different from Example 1 in a shape of the extension unit 3, which is formed on a periphery of the guard unit 2 as extending from the periphery in Example 1. Namely, the difference is that the hat brim shaped extension unit 3 in Example 1 is replaced by a cap brim shaped extension unit 3b in Example 2. A length "e" of a brim of the extension unit 3b shown in FIGS. 8A to 8C is in a range between 0.5 mm and 1.5 mm. A length "e'" of a brim shown in FIGS. 9A to 9C is 1.5 mm. A length "e'" of a brim is 1.0 mm (not shown).

Further, as shown in FIGS. 8A and 9A, it is preferable to arrange the extension unit 3b so that an angle α formed by an imaginable axis "c" of the facial nerve root H2 contacting to the recess shaped portion 2c and a center line of the extension unit 3b, is to be 60 to 90 degrees. The arrangement is based on patient variations. Hereby, it is possible to apply the electrode part 1 to almost all of patients by preparing different types of the electrode part 1 in which the arrangement of the extension unit 2b is slightly modified.

Hereinafter, details will be explained in reference to more specific examples. Here, if the facial nerve root H2 passes in parallel to the anterior inferior cerebellar artery M, which is a big blood vessel, it is preferable that the angle α is 90 degrees. If the facial nerve root H2 and the anterior inferior cerebellar artery M cross with an angle of 20 degrees, it is preferable that the angle α is 70 degrees. Further, if the facial nerve root H2 and the anterior inferior cerebellar artery M cross with an angle of 40 degrees, it is preferable that the angle α is 50 degrees. As mentioned above, the arrangement of the extension unit 3b is performed as the case may be.

Furthermore, as shown in FIGS. 8C and 9C, a marking 2d is attached or carved on the guard unit 2. The marking 2d is a line marker used for adjusting the marker to a direction of an imaginable axis "c", when the electrode part 1 is held.

Figure 10A:
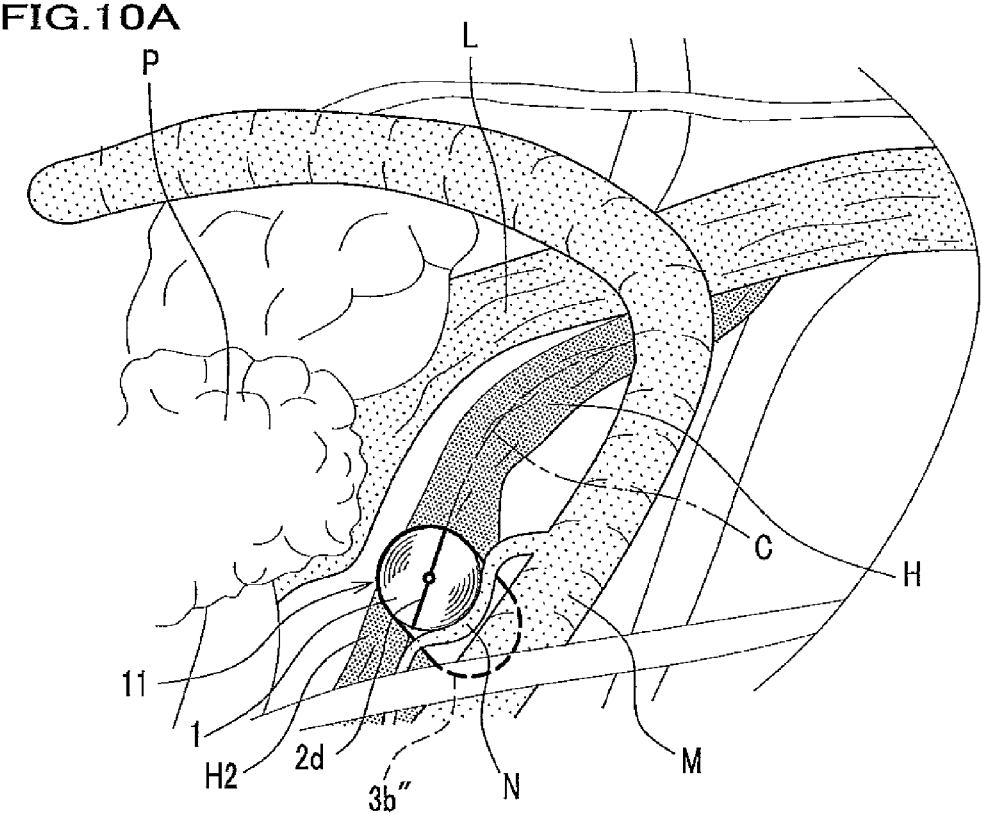
FIGS. 10A and 10B are diagrams showing another example of the electrode for continuously stimulating the facial nerve root of the present invention, respectively. Both diagrams show a state that the electrode for continuously stimulating the facial nerve root is fixed.

As shown in FIG. 10A, the extension unit 3b" is inserted to a vicinity of the facial nerve root H2 where the facial nerve root H2 and the anterior inferior cerebellar artery M cross or come close each other. In this way, the electrode part 1 is held. The holding process is the same as described in Example 1.

<Holding Method of Electrode Part>

As shown in FIG. 10A, a holding method of the electrode part 1 of the electrode for continuously stimulating the facial nerve root 11 comprises steps of, adjusting a line of the marking 2d parallel to an imaginable axis "c" of the facial nerve root H2, and holding the extension unit 3b" between a root of the facial nerve H just coming out of the brainstem F, that is, the facial nerve root H2, and the anterior inferior cerebellar artery M of a big blood vessel, or between the facial nerve root H2 and the small artery N of a small blood vessel, so that the electrode part 1 is fixed.

As mentioned above, in place of a hat brim shaped extension unit 3 formed on a whole circumferential periphery of the guard unit 2 as extending from the periphery thereof shown in FIG. 6, the electrode part 1 having a cap brim shaped extension unit 3b" formed on a part of the circumferential periphery of the guard unit 2, can be fixed.

Hereby, it is possible to fix the electrode part 1 by holding it between the facial nerve root H2 coming out of the brainstem F and the anterior inferior cerebellar artery M. As a result, stable and excellent measurement of electromyogarphic potentials with significantly reduced background noises can be realized.

Figure 10B:
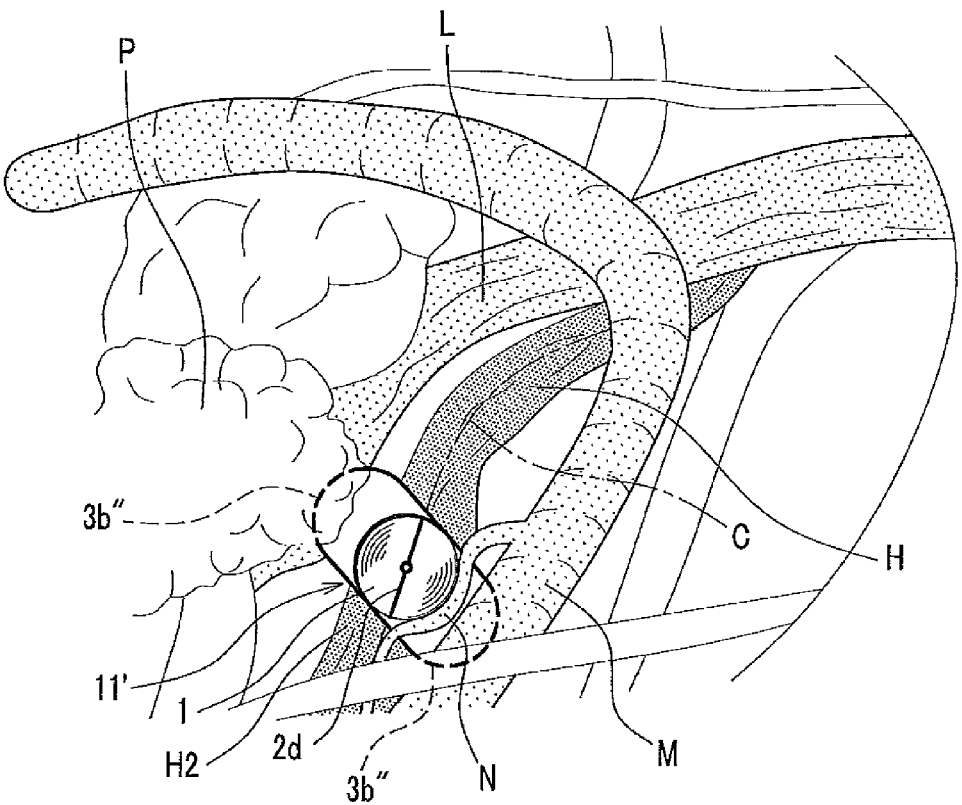

Here, as shown in FIG. 10B, an additional cap brim shaped extension unit 3b" can be arranged in the electrode part 1. The additional cap brim shaped extension unit 3b" may be inserted between the auditory nerve L and the choroid plexus P producing cerebrospinal fluid. This type of the holding method can be also applicable.

Figure 11A:
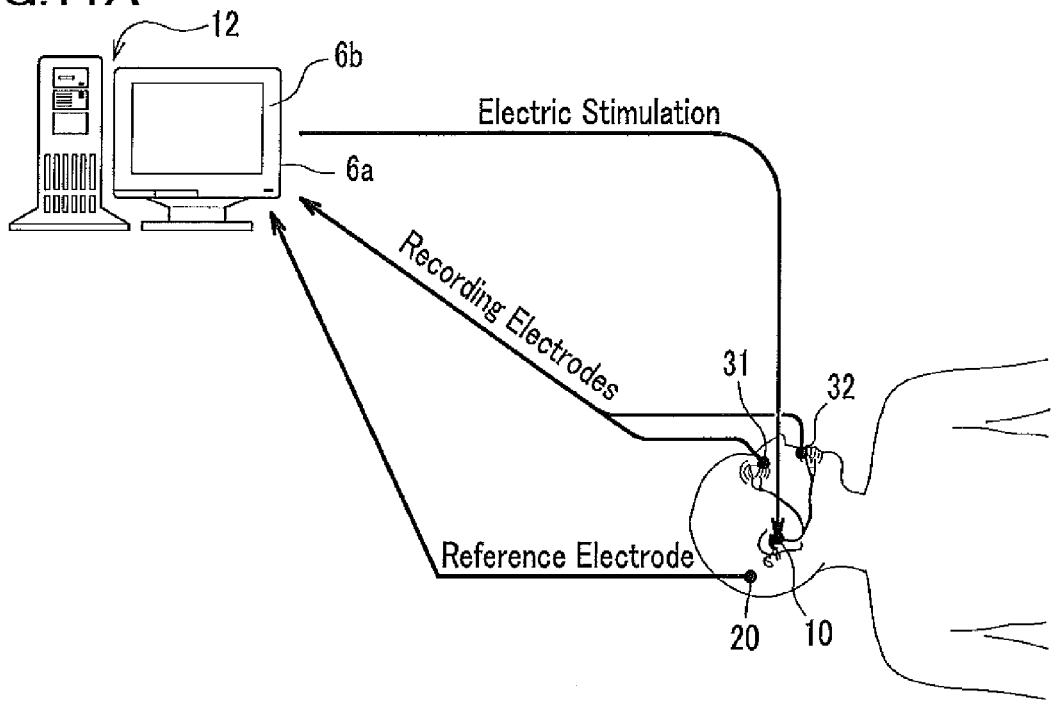
FIG. 11A is a schematic diagram showing a whole system constitution of the apparatus for monitoring electromyograms of facial muscles using the electrode for continuously stimulating the facial nerve root.
Figure 11B:
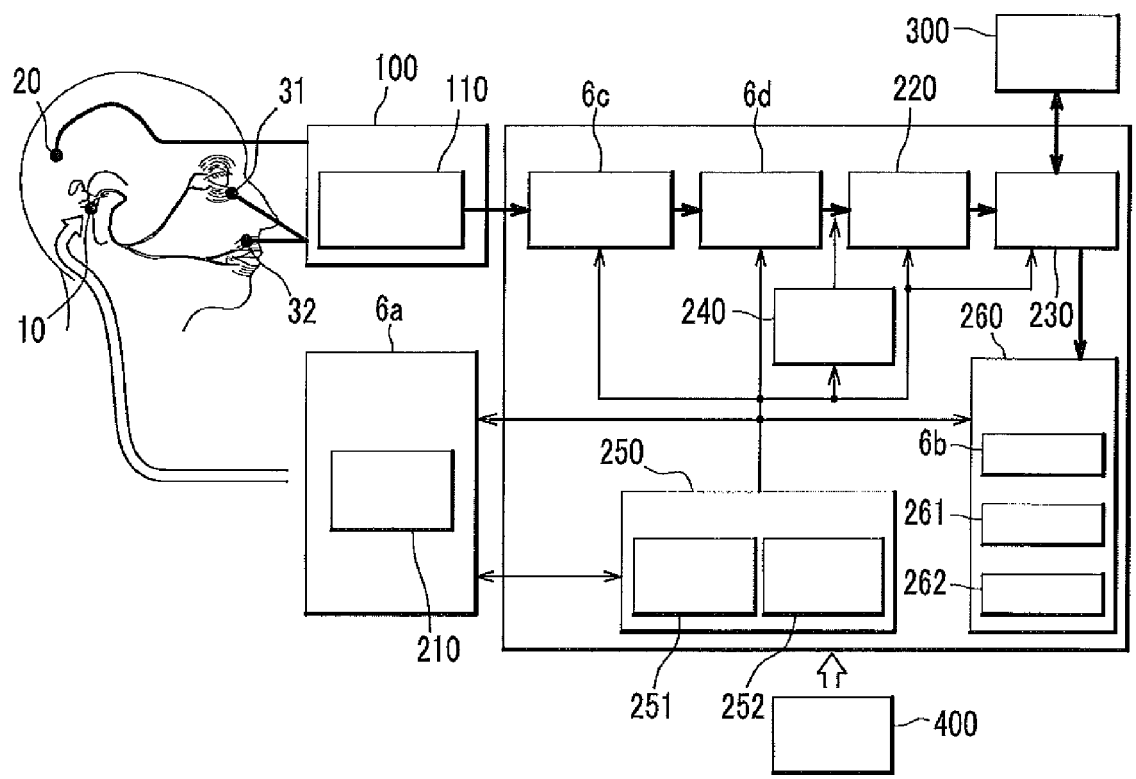
FIG. 11B is a block diagram showing constitution of the apparatus thereof using the electrode for continuously stimulating the facial nerve root.

As shown in FIGS. 11A and 11B, an apparatus for monitoring electromyograms of facial muscles 12 comprises the electrode for continuously stimulating the facial nerve root 10, an electric stimulus means (or called stimulus unit) 6a which stimulates the facial nerve root of patients on whom the electrode for continuously stimulating the facial nerve root 10 is held, a display means (or called display) 6b which displays potentials evoked by the electrode for continuously stimulating the facial nerve root 10, a control unit 250 which controls the electric stimulus means (or called stimulus unit) 6a and the display means (or called display) 6b, an input means (or called input box) 100, a reference electrode 20, and recording electrodes 31 and 32 which measure muscle contraction responses elicited by continuously stimulating the facial nerve root. Herein, the electrode for continuously stimulating the facial nerve root 10 is electrically connected to the electric stimulus means 6a. The reference electrode 20 and the recording electrodes 31 and 32 are electrically connected to the input means 100. Further, the apparatus for monitoring electromyograms of facial muscles 12 comprises an amplifier 6c which deletes background electromyograms mixing in the same phase, and an A/D converter 6d which converts an analogue signal amplified by the amplifier 6c to a digital signal.

The electric stimulus means 6a generates electric stimulation 210 of 1 to 3 Hz frequencies and stimulates the facial nerve root H2 by generating stimulus electric currents for the facial nerve root H2. The electric stimulus means 6a is electrically connected to the control unit 250. Preferably, the electric stimulus currents are in a range between 0.1 mA and 2.0 mA.

Next, referring to FIG. 11B, more detailed constitution will be explained hereinafter. FIG. 11B is a block diagram showing constitution of the apparatus for monitoring electromyograms of facial muscles 12 using the electrode for continuously stimulating the facial nerve root 10.

<Constitution of Impedance Converter>

An impedance converter 110 of an input means 100 reduces a load of an amplifier 6c through an impedance conversion. If the amplifier 6c with sufficiently low impedance is not used, a signal generated by a bioelectric phenomenon such as an electromyogram is liable to be distorted.

In this regard, in order to reduce a signal source resistor in case that the amplifier 6c is applied to a living body, it is needed to reduce a load of the amplifier 6c by using the impedance converter 110. It is preferable that an impedance conversion is performed near the electrode 10 as close as possible. As mentioned above, electromyographic potential differences of facial muscle contractions measured between the reference electrode 20 and the recording electrodes 31 and 32 both from orbicularis oculi muscle and orbicularis oris muscle are inputted into the impedance convertor 110 of the input means 100.

<Constitution of Amplifier>

An amplifier 6c in FIG. 11B is a differential amplifier. Signals of the potential differences outputted from the impedance converter 110 are amplified in a predetermined amplified rate by the differential amplifier 6c. At this time, background electromyograms mixing in the same phase as the electromyograms of the facial muscle contractions detected by the reference electrode 20 and the recording electrodes 31 and 32 both from orbicularis oculi muscle and orbicularis oris muscle, are deleted by the amplifier 6c. Hereby, electromyograms of spontaneous discharge mixing in the same phase are deleted. Output of the differential amplifier 6c extracts required components of the electromyograms through a filter circuit (not shown), and reduces unnecessary components such as background electromyograms of spontaneous discharge.

<Constitution of A/D Converter>

Output of the amplifier 6c is a continuous electric signal of an amplified electromyogram. An A/D converter 6d converts the continuous analogous electric signal to a digital signal.

<Constitution of Excessive Input Eliminating Unit>

An excessive input eliminating unit 240 eliminates an excessive input from signal data which is to be processed in adding and averaging processing, if there is the excessive input mixing in the signal data.

<Constitution of Adding Unit>

An adding unit 220 is a circuit to perform adding and averaging processing for the digital signal converted by the A/D converter 6b and input from the excessive input eliminating unit 240, so as to reduce background electromyograms of spontaneous discharge mixing in the detection signal.

<Constitution of Data Memory>

A data memory 230 stores data generated by the excessive input eliminating unit 240 and the adding unit 220. Optionally, the data memory 230 is connected to an outside storage 300.

<Constitution of Output Unit>

An output unit 260 includes a display 6b, a recording unit 261, and outside output 262.

<Constitution of Display>

Figure 12A:
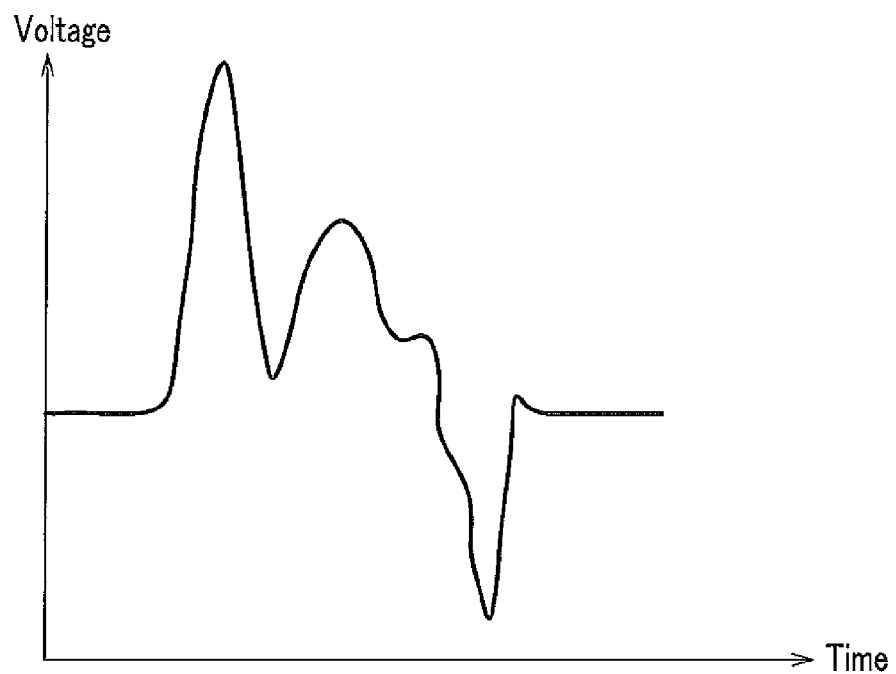
FIGS. 12A and 12B show waveforms displayed on the monitoring display.
Figure 12B:
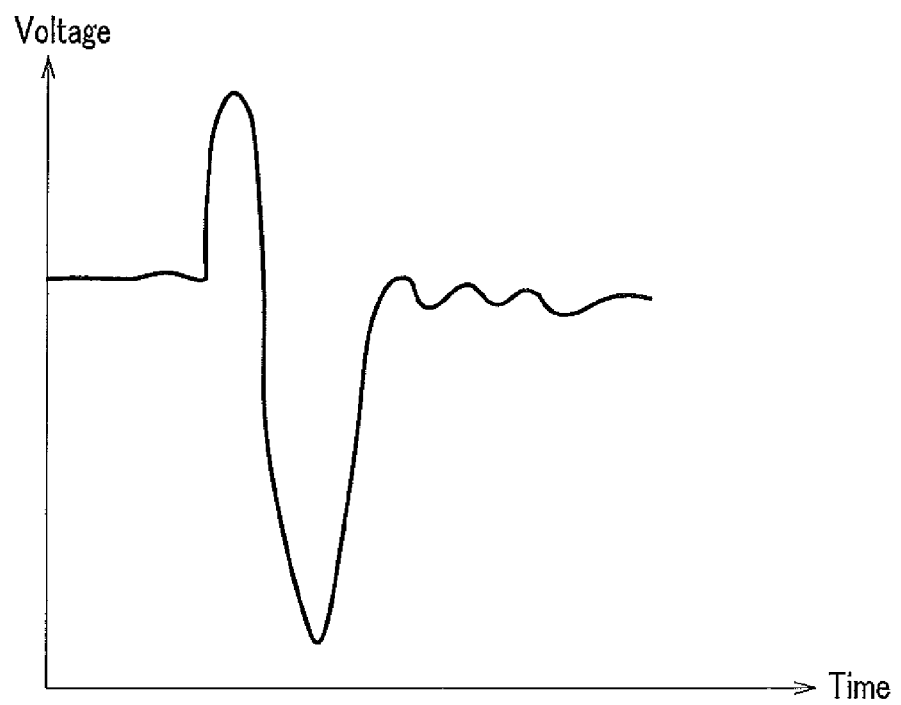
Figure 13:
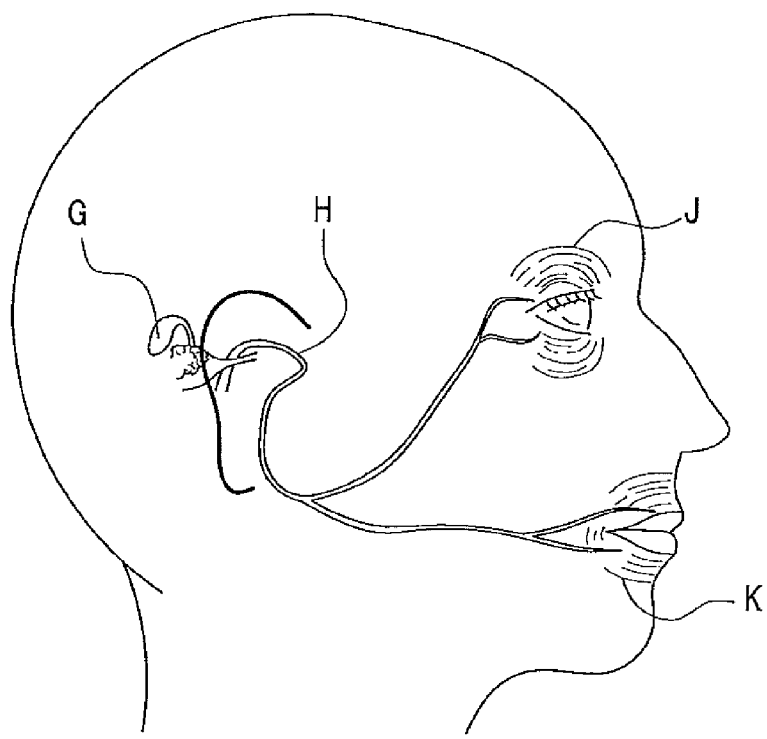
FIG. 13 is a schematic diagram showing the facial nerve extending four branches to the human facial muscles.
Figure 14:
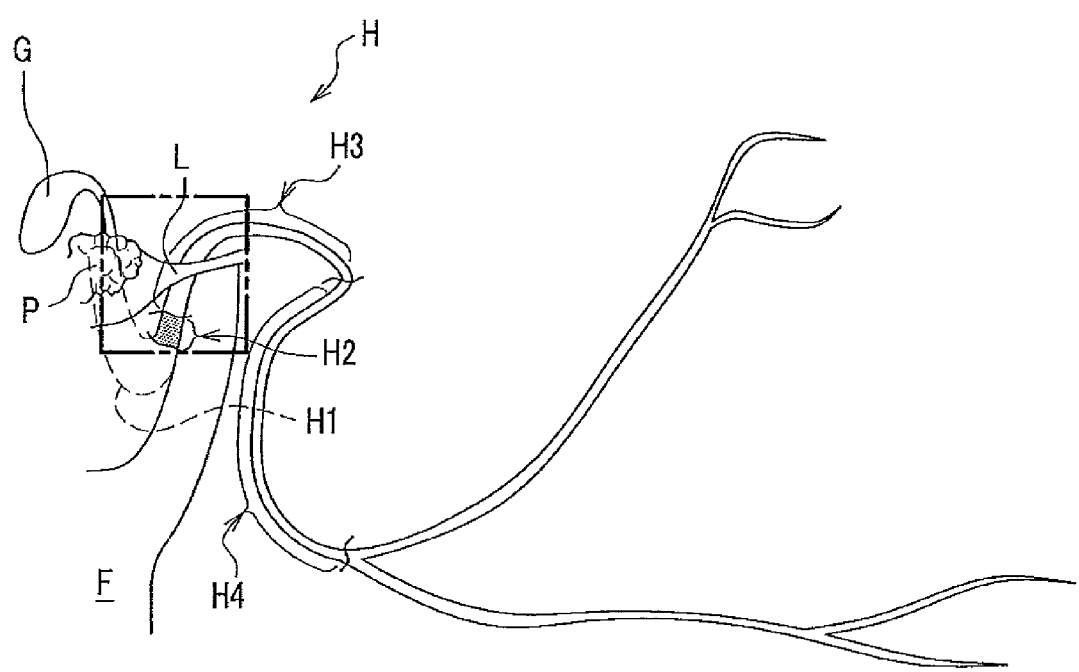
FIG. 14 is an enlarged diagram of FIG. 13 showing the facial nerve root H2.
Figure 15:
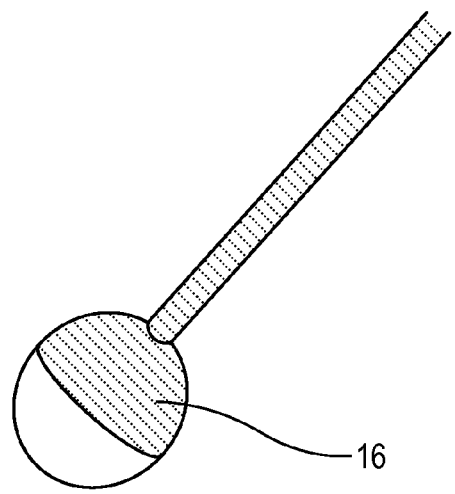
FIG. 15 is a perspective view of a conventional bell shaped electrode.
Figure 16:
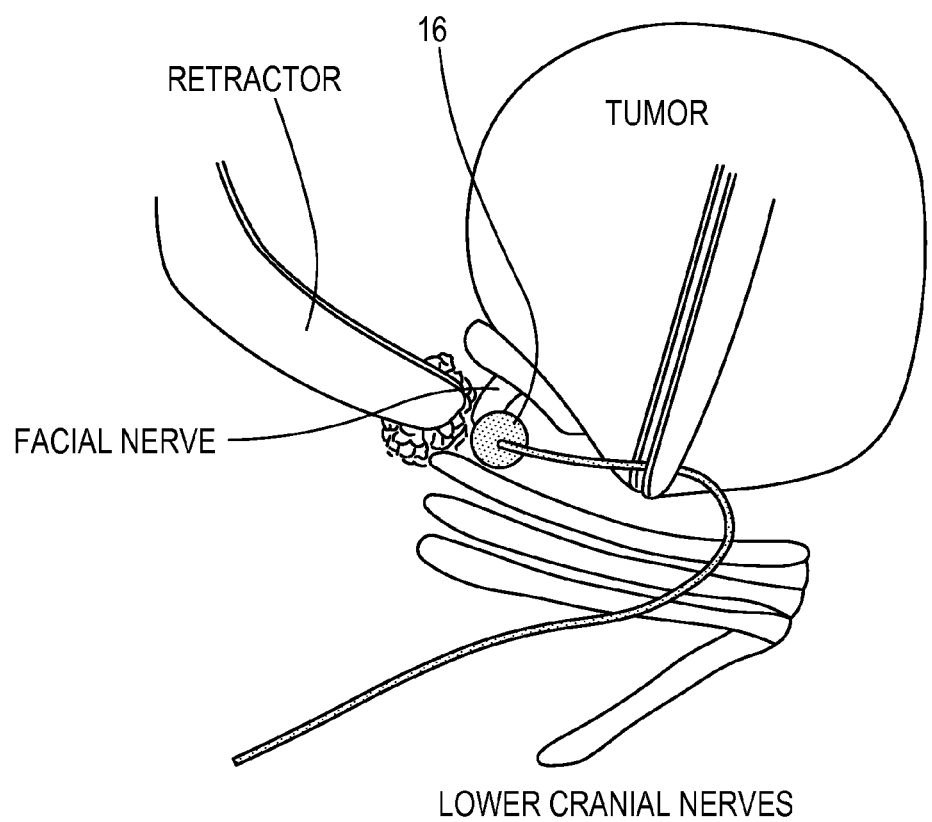
FIG. 16 is an explanatory diagram showing a state that the conventional bell shaped electrode is placed in a tumor operation.

A display 6b of the display means is a liquid crystal screen as shown in FIG. 11A. As shown in FIGS. 12A and 12B, the display 6b displays a graph of electromyographic potentials, in which a vertical axis represents a voltage and a horizontal axis represents a time. A switch is provided on the display 6b for turning on and turning off, and a selection of amplitude is possible. The display 6b of the display means, which is a liquid crystal screen, is electrically connected to the control unit 250 as shown in FIG. 11B. The liquid crystal display screen is a display of a digital computer, on which an input waveform, condition configuration, and a processing state of a detected signal by the recording electrodes 31 and 32 both from orbicularis oculi muscle and orbicularis oris muscle, can be displayed.

<Constitution of Recording Unit>

A recording unit 261 is a universal printer for printing data displayed on the display 6b, preferably, an inkjet printer and a laser printer.

<Constitution of Electric Stimulus Means>

An electric stimulus means 6a generates an electric stimulation 210.

<Constitution of Control Unit>

A control unit 250 comprises CPU (central processing unit of a computer) 251 and a program memory 252. The control unit 250 is a unit for driving the electric stimulus means 6a and the display 6b based on an input signal from the input means 100, and is electrically connected to a power source 400 (not shown). The control unit 250 has functions for amplifying weak potentials evoked by the electrode for continuously stimulating a facial nerve root 10 and driving the display 6b. Further, the control unit 250 is a unit for driving the electric stimulus means 6a and the display 6b based on an input signal from the input means 100, and is electrically connected to a power source 400 not shown.

Accordingly, by introducing the new monitoring method and feedback system using the electrode for continuously stimulating the facial nerve root 10, the following outstanding effect is achieved. That is, it is possible to change a procedure location, a procedure speed and a procedure method according to results obtained by the monitoring. Actually, even for an operation of acoustic neuromas which has been regarded to be significantly difficult, it is possible to morphologically and functionally preserve the facial nerve H, in almost 95% and 90% probabilities, respectively.

As described above, if the apparatus for monitoring electromyograms 12 using the electrodes for continuously stimulating the facial nerve root 10 and 11 is evaluated in comparison with conventional monitoring apparatuses, it is evident that a performance of the apparatus for monitoring electromyograms 12 of the present invention is greatly improved, in stability, adherent property, and comprehensiveness. For example, in case of a conventional electrode for continuously stimulating a facial nerve, it has not been possible to tightly fix the conventional electrode only by dwelling it during an operation. On the contrary, in case of the electrode of the present invention, it is possible to perform a real time monitoring even for a facial nerve root H2 because of the highly stable holding method of the electrode of the present invention, which is incomparable to the holding method using the conventional electrode. Hereby, it is possible to specifically and sensitively observe electromyographic potentials of the facial muscles, in highly frequent, highly specific, and highly sensitive conditions. As a result, functional preservation of the facial nerve H is greatly improved.

Here, the present invention is not limited to the above mentioned embodiments. Alternation and modification of the embodiments are possible in the same technological idea. For example, in the present embodiments, it has been described that the electrode for continuously stimulating the facial nerve root 10 is formed as a cone shape having a diameter "φ" 2.5 mm, and a height "h" of 2.0 mm. However, the size is not limited to the above mentioned size, and a larger or a smaller size than the above mentioned size may be appropriate. Further, the shape of the extension unit 3 is not limited to the shape described in the embodiments, and other shapes can be appropriate, as long as the shape is a brim typed shape.

Further, it has been described that the shape of the electrode unit 1a is oval or elliptical in addition to circular. However, the shape of the electrode unit 1a can be rectangular or triangular, and other shapes can be used.

Further, it has been described that with respect to materials, the electrode unit 1a is made of platinum and the recess shaped portion 2c of the contact unit 2b is made of gold (Au). Herein, the electrode unit 1a and the recess shaped portion 2c can be made of gold formed as a recess shaped gold plate. Here, gold can be replaced by conductive silicon that is a biocompatible resin.

Further, as shown in FIG. 10A, it has been described that the cap shaped extension unit 3b" is arranged on the outer periphery of the guard unit 2 as extending in one direction. Alternatively, the cap shaped extension unit 3b" can be arranged as extending in two directions as shown in FIG. 10B.

Furthermore, it has been described that the marking 2d is a line shaped marker provided on the guard unit 2. However, a dotted line shaped marker can be used, and the marking 2d can be provided on the extension units 3 and 3b, in place of or in addition to the guard unit 2.

What is claimed is:

1. An electrode for continuously stimulating a facial nerve root, which electrically stimulates the facial nerve root that is a root of a facial nerve extending from a facial nucleus in a brainstem, in order to monitor electromyograms of contraction responses of an orbicularis oculi muscle and an orbicularis oris muscle which are regulated by the facial nerve, the electrode for continuously stimulating the facial nerve root comprising:

an electrode unit configured to receive currents electrically stimulating the facial nerve root, the electrode unit consisting of a single electrode;

a contact unit electrically connected to the electrode unit and configured to contact the facial nerve root;

a guard unit configured to cover the electrode unit and expose the contact unit, wherein the guard unit is formed in a conical shape;

an extension unit formed in a washer shape and configured to extend From a periphery of the guard unit;

a handle configured to be a bar shaped unit provided on a top of the guard unit and Configured to facilitate the electrode to be inserted and held; and a wire unit, wherein the extension unit is configured to be held by being clamped between the facial nerve root coming out of the brainstem and an anterior inferior cerebellar artery crossing the facial nerve root, and the contact unit is configured to be fixed to the facial nerve root.

2. The electrode for continuously stimulating the facial nerve root according to claim 1, wherein the extension unit is made of silicon.

3. The electrode for continuously stimulating the facial nerve root according to claim 1, wherein the contact unit is formed in a flat shape corresponding to an outer peripheral surface of the facial nerve root.

4. An apparatus for monitoring electromyograms of facial muscles using an electrode for continuously stimulating a facial nerve root, the apparatus comprising:

the electrode for continuously stimulating the facial nerve root as claimed in claim 1;

an electric stimulus unit configured to stimulate the facial nerve root of a patient on whom the electrode for continuously stimulating the facial nerve root is held;

a recording electrode configured to measure muscle contraction responses elicited by continuously stimulating the facial nerve root; and a display configured to display muscle contraction responses of an orbicularis oculi muscle and an orbicularis oris muscle which are regulated by a facial nerve stimulated by the electrode for continuously stimulating the facial nerve root.

5. An apparatus for monitoring electromyograms of facial muscles using an electrode for continuously stimulating a facial nerve root, the apparatus comprising:

the electrode for continuously stimulating the facial nerve root as claimed in claim 2;

an electric stimulus configured to stimulate the facial nerve root of a patient on whom the electrode for continuously stimulating the facial nerve root is held;

a recording electrode configured to measures muscle contraction responses elicited by continuously stimulating the facial nerve root; and a display configured to display muscle contraction responses of an orbicularis oculi muscle and an orbicularis oris muscle which are regulated by a facial nerve stimulated by the electrode for continuously stimulating the facial nerve root.

6. An apparatus for monitoring electromyograms of facial muscles using an electrode for continuously stimulating a facial nerve root, the apparatus comprising:

the electrode for continuously stimulating the facial nerve root as claimed in claim 3;

an electric stimulus means which stimulates the facial nerve root of a patient on whom the electrode for continuously stimulating the facial nerve root is held;

a recording electrode which measures muscle contraction responses elicited by continuously stimulating the facial nerve root; and a display configured to display muscle contraction responses of an orbicularis oculi muscle and an orbicularis oris muscle which are regulated by a facial nerve stimulated by the electrode for continuously stimulating the facial nerve root.

* * * * *